United States Patent
Afzali-Ardakani et al.

(10) Patent No.: US 8,917,096 B2
(45) Date of Patent: Dec. 23, 2014

(54) DETERMINATION OF ISOELECTRIC POINTS OF BIOMOLECULES USING CAPACITIVE SENSORS

(71) Applicant: International Business Machines Corporation, Armonk, NY (US)

(72) Inventors: Ali Afzali-Ardakani, Ossining, NY (US); Christopher P. D'Emic, Ossinging, NY (US); Ashish Jagtiani, Irvington, NY (US); Sufi Zafar, Briarcliff Manor, NY (US)

(73) Assignee: International Business Machines Corporation, Armonk, NY (US)

( * ) Notice: Subject to any disclaimer, the term of this patent is extended or adjusted under 35 U.S.C. 154(b) by 161 days.

(21) Appl. No.: 13/678,118

(22) Filed: Nov. 15, 2012

(65) Prior Publication Data

US 2014/0132275 A1    May 15, 2014

(51) Int. Cl.

| | |
|---|---|
| G01R 27/26 | (2006.01) |
| G01F 7/00 | (2006.01) |
| G01N 19/00 | (2006.01) |
| G01N 27/26 | (2006.01) |
| G01R 1/00 | (2006.01) |
| G01N 27/416 | (2006.01) |
| G01N 27/22 | (2006.01) |
| G06F 3/044 | (2006.01) |
| G01D 5/24 | (2006.01) |

(52) U.S. Cl.
CPC ............... *G01N 27/221* (2013.01); *G01D 5/24* (2013.01); *G01R 1/00* (2013.01); *G01N 27/4167* (2013.01); *G01R 27/26* (2013.01); *G06F 3/044* (2013.01)
USPC .......... 324/438; 324/658; 702/47; 73/335.04; 205/792

(58) Field of Classification Search
CPC ... G01N 27/4167; G01N 27/221; G01R 1/00; G01R 27/26; G06F 3/044; G01D 5/24
USPC ................. 324/438, 658, 663, 672, 679, 686; 205/792; 702/47, 52; 73/335.04, 780, 73/862.337, 862.626, 304 C, 514.32, 718, 73/724
See application file for complete search history.

(56) References Cited

U.S. PATENT DOCUMENTS

| | | |
|---|---|---|
| 6,254,754 B1 | 7/2001 | Ross et al. |
| 7,704,360 B2 | 4/2010 | Sobek et al. |
| 7,785,533 B2 | 8/2010 | Fujita et al. |
| 7,914,656 B2 | 3/2011 | Bukshpan et al. |
| 2007/0231211 A1 | 10/2007 | Yoo et al. |
| 2011/0139637 A1* | 6/2011 | Ah et al. .................. 205/792 |

OTHER PUBLICATIONS

C-G. Ahn et al., "Modified ISFETs having an Extended Gate on the Thick Dielectric," 2009 IEEE Sensors, Oct. 25-28, 2009; pp. 371-374.

(Continued)

*Primary Examiner* — Patrick Assouad
*Assistant Examiner* — Farhana Hoque
(74) *Attorney, Agent, or Firm* — Cantor Colburn LLP; Vazken Alexanian (57) ABSTRACT

A mechanism is provided for determining an isoelectric point of a molecule. A first group of capacitance versus voltage curves of a capacitor is measured. The capacitor includes a substrate, dielectric layer, and conductive solution. The first group of curves is measured for pH values of the solution without the molecule bound to a functionalized material on the dielectric layer of the capacitor. A second group of capacitance versus voltage curves of the capacitor is measured when the molecule is present in the solution, where the molecule is bound to the functionalized material of the dielectric layer of the capacitor. A shift is determined in the second group of curves from the first group of curves at each pH value. The isoelectric point of the molecule is determined by extrapolating a pH value corresponding to a shift voltage being zero, when the shift is compared to the pH values.

5 Claims, 7 Drawing Sheets

(56) References Cited

OTHER PUBLICATIONS

P. Bataillard et al., "Direct Detection of Immunospecies by Capacitance Measurements," Anal. Chem., vol. 60, No. 21, 1988, pp. 2374-2379.

P. Bergveld, "A Critical Evaluation of Direct Electrical Protein Detection Methods," Biosensors and Bioelectronics, vol. 6, Issue 1, 1991, pp. 55-72.

B. Reddy Jr., "Nanoscale BioFETs for Ulrasensitive pH and Bimolecular Detection," Ph.D. Thesis, University of Illinois at Urbana-Champaign, May 22, 2012; 180 pages.

\* cited by examiner

DETERMINATION OF ISOELECTRIC POINTS OF BIOMOLECULES USING CAPACITIVE SENSORS

BACKGROUND

The present invention relates to biomolecules, and more specifically, to determining isoelectric points of biomolecules using capacitive sensors.

Figure 1:
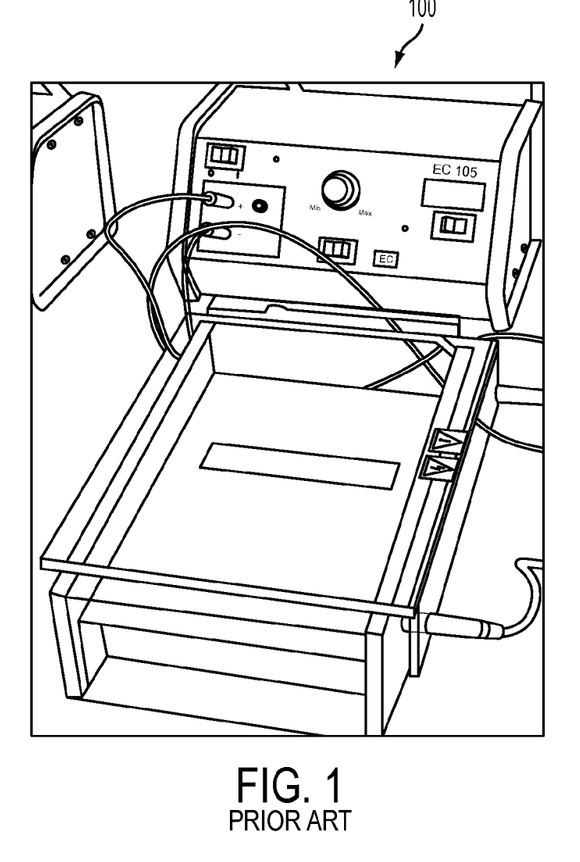
FIG. 1 illustrates a typical method and setup for determining the isoelectric point based on electrophoresis.

The isoelectric point of biomolecules is defined as the pH at which the net charge on the biomolecule is zero. It is a main property of proteins which plays an important role in purification and solubility. The isoelectric point is also used as an identification marker for proteins. FIG. 1 illustrates a typical method and setup for determining the isoelectric point is based on electrophoresis. In FIG. 1, the typical apparatus requires high voltages (>50V), is time consuming (~2 to 16 hours), and is therefore expensive. The typical apparatus is approximately 1 square foot for measuring the isoelectric point.

SUMMARY

According to an embodiment, a method of determining an isoelectric point of a target molecule. The method includes measuring a first plurality of capacitance versus voltage curves of a capacitor. The capacitor includes a substrate, a dielectric layer, and an electrically conductive solution. The first plurality of capacitance versus voltage curves are measured for a plurality of pH values of the electrically conductive solution without the target molecule being bound to a functionalized material on the dielectric layer of the capacitor. The method includes measuring a second plurality of capacitance versus voltage curves of the capacitor when the target molecule is present in the electrically conductive solution, where the target molecule is bound to a functionalized material of the dielectric layer of the capacitor. The method includes determining a shift in the second plurality of capacitance versus voltage curves from the first plurality of capacitance versus voltage curves at each of the plurality of pH values, and determining the isoelectric point of the target molecule by extrapolating a pH value that corresponds to a shift voltage being zero, when the shift at a plurality of shift voltages is compared to the plurality of pH values.

According to an embodiment, a system for determining an isoelectric point of a target molecule. The system includes a dielectric layer disposed on a substrate, a functionalized material on the dielectric layer, and an electrically conductive solution on the dielectric layer. The substrate, the dielectric layer, and the electrically conductive solution form a capacitor. The system includes a first contact in the electrically conductive solution and a second contact on the substrate. A first plurality of capacitance versus voltage curves of the capacitor are measured via the first contact and the second contact. The first plurality of capacitance versus voltage curves are measured for a plurality of pH values of the electrically conductive solution without the target molecule being present in the electrically conductive solution of the capacitor. A second plurality of capacitance versus voltage curves of the capacitor are measured via the first contact and the second contact when the target molecule is present in the electrically conductive solution, where the target molecule is bound to the functionalized material on a top surface of the dielectric layer of the capacitor. A shift in the second plurality of capacitance versus voltage curves from the first plurality of capacitance versus voltage curves is determined at each of the plurality of pH values via test equipment. The isoelectric point of the target molecule is determined via the test equipment by extrapolating a pH value that corresponds to a shift voltage being zero, when the shift at a plurality of shift voltages is compared to the plurality of pH values.

According to an embodiment, a non-transitory computer program product for determining an isoelectric point of a target molecule. The computer program product comprising a computer readable storage medium having program code embodied therewith. The program code executable by a processing circuit to perform a method including measuring a first plurality of capacitance versus voltage curves of a capacitor, where the capacitor includes a substrate, a dielectric layer, and an electrically conductive solution. The first plurality of capacitance versus voltage curves are measured for a plurality of pH values of the electrically conductive solution without the target molecule being present in the electrically conductive solution of the capacitor. The method includes measuring a second plurality of capacitance versus voltage curves of the capacitor when the target molecule is present in the electrically conductive solution, where the target molecule is bound to a top surface of the dielectric layer of the capacitor. The method includes determining a shift in the second plurality of capacitance versus voltage curves from the first plurality of capacitance versus voltage curves at each of the plurality of pH values, and determining the isoelectric point of the target molecule by extrapolating a pH value that corresponds to a shift voltage being zero, when the shift at a plurality of shift voltages is compared to the plurality of pH values.

Additional features and advantages are realized through the techniques of the present invention. Other embodiments and aspects of the invention are described in detail herein and are considered a part of the claimed invention. For a better understanding of the invention with the advantages and the features, refer to the description and to the drawings.

BRIEF DESCRIPTION OF THE SEVERAL VIEWS OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

DETAILED DESCRIPTION

An embodiment of the present invention provides a capacitive technique using blanket dielectric films deposited on silicon as a sensor capacitor device for measuring the isoelectric point of the target molecule. The capacitive sensor technique is fast, inexpensive, and miniaturized (e.g., only a few mm² area). Also, the sensor device uses low voltage (<1.5V) and requires a small protein sample volume (<30 μL). This sensor can be easily integrated with CMOS (complementary metal oxide semiconductor) technology to make a portable and low powered device for measuring isoelectric point.

The embodiment demonstrates an alternative method for measuring the isoelectric point of proteins using blanket $SiO_2/HfO_2$ films grown on silicon as dielectric layers. Other dielectric layers can also be used. The isoelectric point is measured by measuring before and after the target molecule is bound to the dielectric surface. The method is sensitive, inexpensive, and miniaturized.

Figure 2:
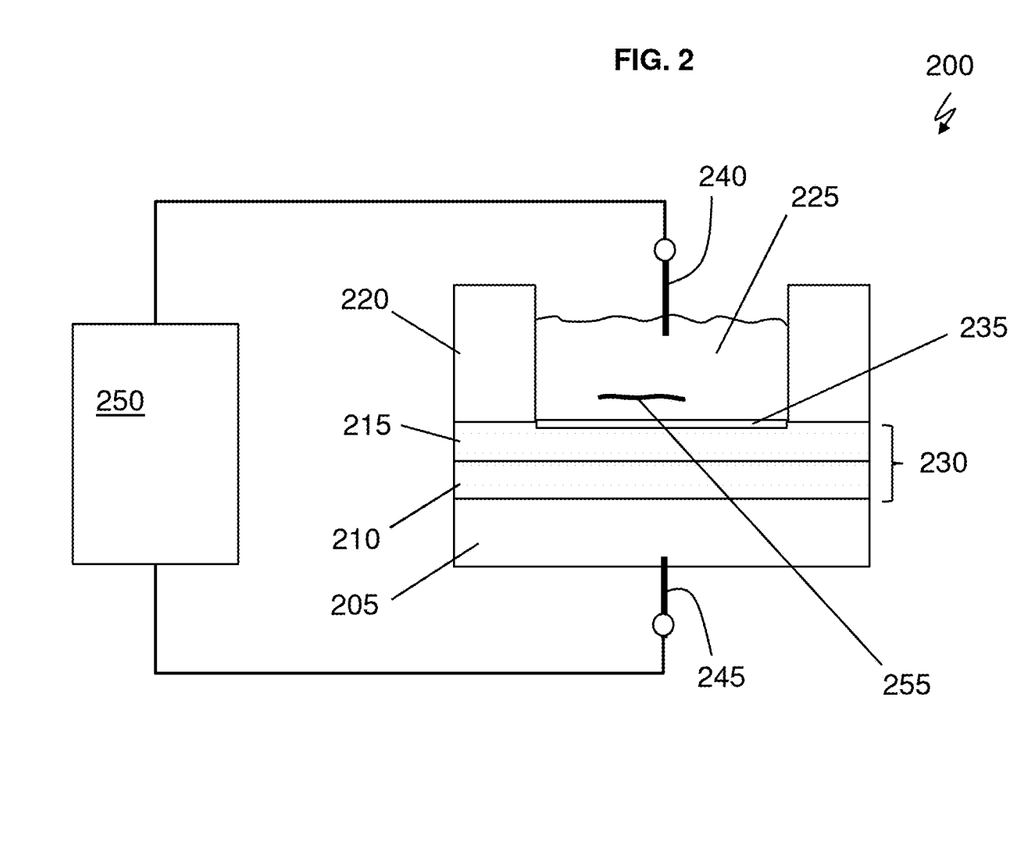
FIG. 2 is a cross-sectional view of a capacitor device according to an embodiment.

Now turning to the figures, FIG. 2 is a cross-sectional view of a capacitor device 200 according to an embodiment. The device 200 is and operates as a capacitor. When a molecule is in the device 200, the device 200 can operate as a sensor to determine the isoelectric point of the molecule as discussed herein.

The device 200 includes a substrate 205. The material for the substrate 205 may include silicon (Si). A dielectric layer 210 may be deposited on the substrate 205. In one case, the dielectric layer 210 may be grown on the silicon substrate 205, and the dielectric layer 210 may include silicon dioxide ($SiO_2$). In one case, another dielectric layer 215 may be deposited on the dielectric layer 210. The dielectric layer 215 may be hafnium oxide ($HfO_2$). Further, dielectric layer 230 shows that the same dielectric material (e.g., a single dielectric film) or different materials (e.g., more than one dielectric film) may be utilized. For example, the dielectric layer 230 may be $SiO_2$, $HfO_2$, $Al_2O_3$, and/or or bilayers of two different dielectric films. In an experiment discussed herein, a stack of $SiO_2$ (2 nm) and $HfO_2$ (4 nm) was used as the dielectric layer 230, and the $HfO_2$ layer was in contact with electrically conductive solution 225.

Additionally, the dielectric layer 215 may be functionalized with a material 235 that is configured and designed to bind to a target molecule 255 during testing. Further discussion of an example functionalized material 235 and target molecule 255 are discussed herein.

The device 200 includes a holder 220 operatively attached to the dielectric layer 215. The holder 220 may be a plastic container sealed to the dielectric layer 215, and the holder 220 has an opening (at its bottom) to the top surface of the dielectric layer 215. The holder 220 contains the electrically conductive solution 225 with the dielectric layer 215 as the bottom of the holder 220. The electrically conductive solution 225 may be an electrolyte solution (i.e., a buffer solution). During testing, the electrically conductive solution 225 contains the molecule 255 being tested. A contact/electrode 240 is in the electrically conductive solution 225. The contact/electrode 240 and substrate backside contact 245 are connected to electronic equipment 250 for measuring capacitance versus voltage curves.

The dielectric layer 230 on the substrate 205 forms a MOS (metal oxide semiconductor) capacitor device 200 with the solution 225 as the top gate. In the device 200, the electrode 240 capacitance (between contacts 240 and 245) is significantly larger than the dielectric film capacitance.

Figure 3A:
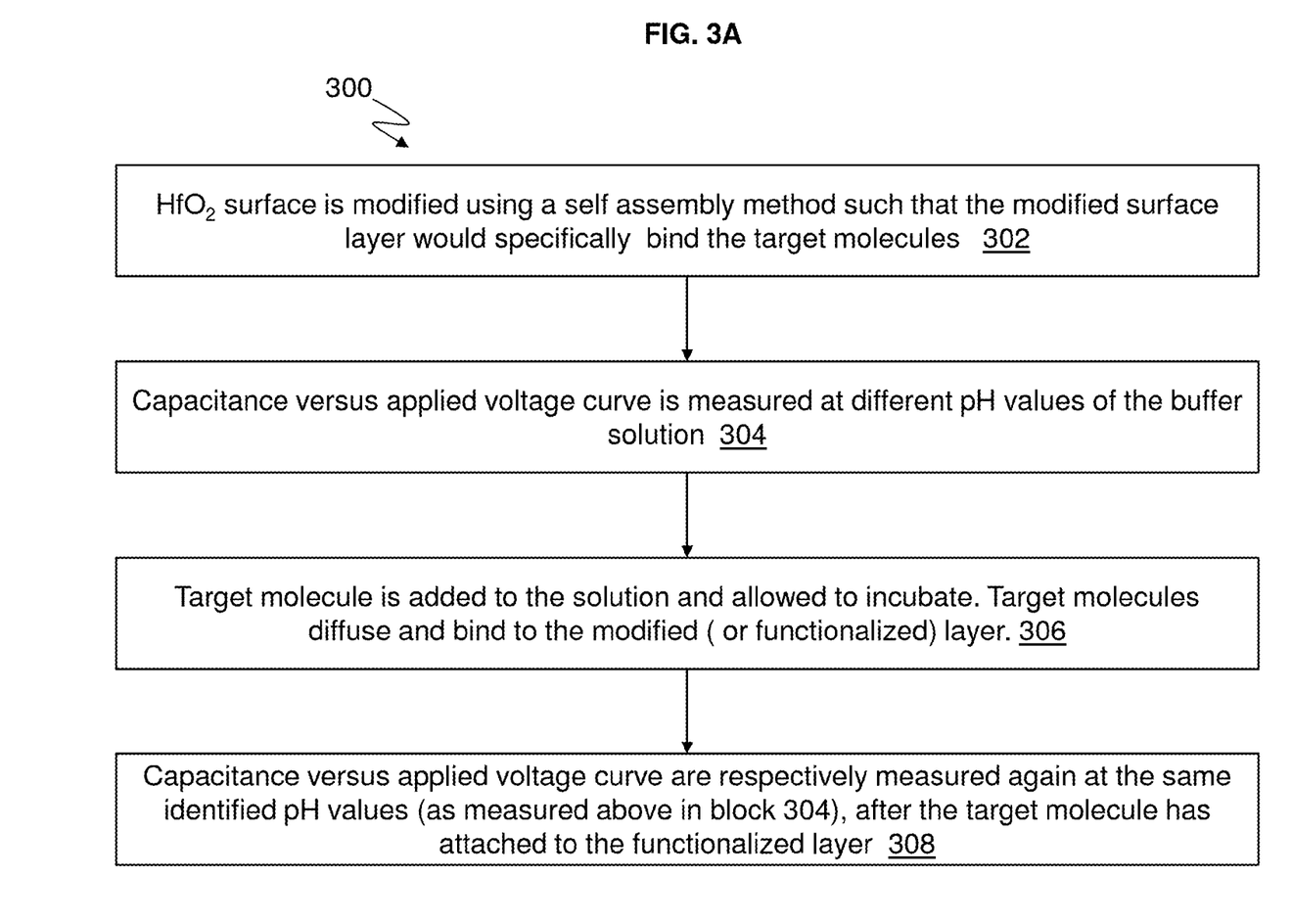
FIGS. 3A and 3B together describe the process flow of the present invention according to an embodiment.
Figure 3B:
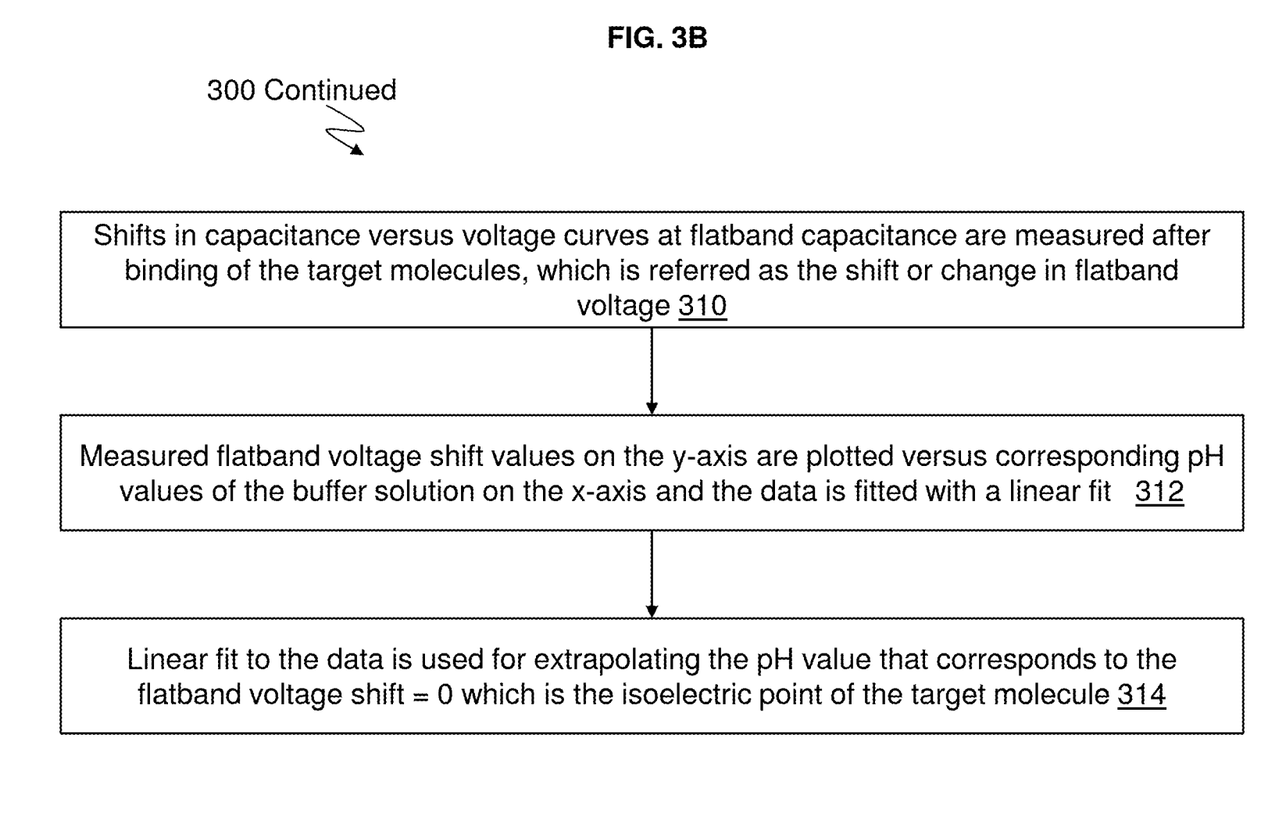

An example is provided to show how to utilize the device 200 as a sensor to determine the isoelectric point of the target molecule 255. For explanation purposes and not limitation, the target molecule 255 is a Neutravidin protein and the functionalized material 235 is biotin because the Neutravidin protein (molecule 255) binds with high specificity to biotin. Turning to FIGS. 3A and 3B, a flow chart 300 is provided for determining the isoelectric point of the molecule 255, which is Neutravidin protein, in the device 200.

Biotin, as the functionalized material 235, is self assembled over the $HfO_2$ surface of the dielectric layer 215 using a self assembly method at block 302. Molecular self-assembly is the process by which molecules adopt a defined arrangement without guidance or management from an outside source.

Bias voltages are applied by the voltage source of the electronic equipment 250 to the electrodes 240 and substrate backside contact 245 connected to the device 200, and the capacitance is measured for each voltage applied. For example, the capacitance versus voltage curve (C-V curves) is measured (via electrodes 240 and 245) across the substrate 205, dielectric layer 210, dielectric layer 215, functionalized material 235, and solution 225 ($Si/SiO_2/HfO_2$/biotin/solution structure) at different pH values (e.g., pH values 6.9, 6.3, 4.7) of the electrically conductive solution 225 at block 304. In other words, the solution 225 is continuously changed to each of the identified pH values, and the capacitance is measured for the range of applied voltages at each pH value. At this time, the target molecule 255 is not in the solution 225.

The Neutravidin protein (target molecule 255) is added to the solution 225 and allowed to incubate for a few minutes at block 306. During this time, the Neutravidin protein (target molecule 255) is diffuses and attaches to the functionalized (biotin) surface 235 that is in contact with the solution 225.

At block 308, the capacitance versus voltage curves (C-V curves) are respectively measured again at the same identified pH values (as measured above in block 304), after the target molecule 255 has attached to the functionalized surface 235. As noted above, the electrically conductive solution 225 is changed to the respective pH values and the capacitance versus voltage curves (C-V curves) are measured at different pH values (e.g., pH values 6.9, 6.3, 4.7) of the solution 225, all while the Neutravidin proteins are bound to the biotin.

Figure 4:
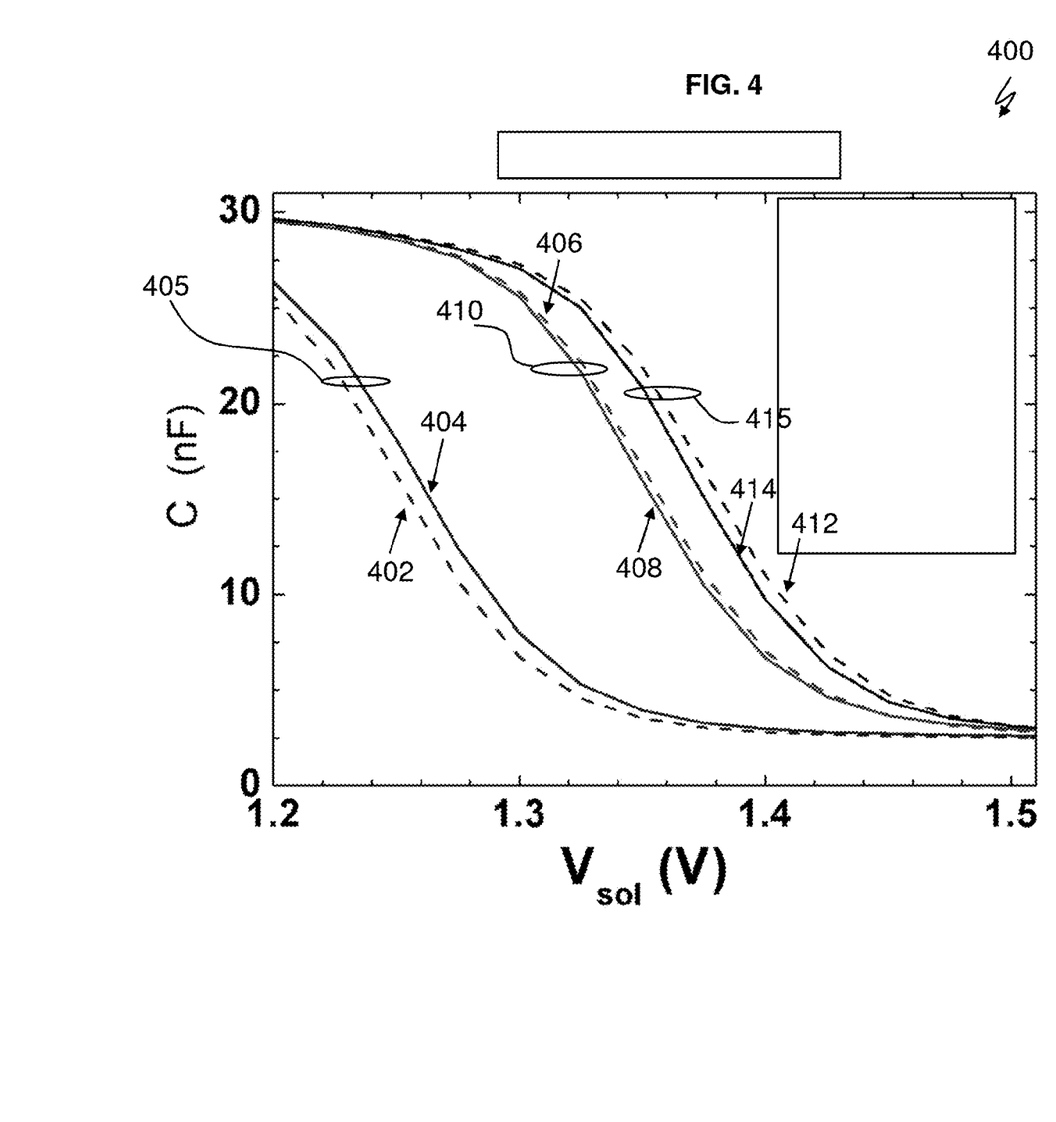
FIG. 4 is a graph of capacitance versus voltage curves at different pH values with and without a molecule present in the device according to an embodiment.

FIG. 4 is a graph 400 of the capacitance versus voltage curves (C-V curves) at each of the pH values as measured by the computer 250. The y-axis shows the measured capacitance (C) in nanofarads (nF). The x-axis shows the applied voltage in volts (V).

The curves 405 are graphed for capacitance measurements made when the solution 225 has a pH value of 4.7. For the two curves 405, the solid line 404 corresponds to the capacitance with biotin (functionalized material 235) covering the dielectric layer 215 without the target molecule 255 bound to the biotin. The dashed line 402 corresponds to capacitance measurements after Neutravidin binding (i.e., the Neutravidin protein molecules bind to the biotin coated surface (i.e., functionalized surface 235)).

The curves 410 are graphed for capacitance measurements made when the solution 225 has a pH value of 6.3. For the two curves 410, the solid line 408 corresponds to the capacitance with biotin (functionalized material 235) covering the dielectric layer 215 without the target molecule 255 present. The dashed line 406 corresponds to the capacitance measurement after Neutravidin binding (i.e., the Neutravidin protein binds to the biotin).

The curves 415 are graphed for capacitance measurements made when the solution 225 has a pH value of 6.9. For the two curves 415, the solid line 414 corresponds to the capacitance with biotin (functionalized material 235) covering the dielectric layer 215. The dashed line 412 corresponds to the capacitance measurement after Neutravidin binding (i.e., the Neutravidin protein binds to the biotin).

In FIG. 4, the graph of C-V curves 405, 410, and 415 (measured by the computer 250 at each respective pH value) shift upon the Neutravidin protein (target molecule 255) binding to biotin (material 235).

When the charge on the Neutravidin protein (target molecule 255) is negative, the shift of the dashed curve (e.g., dashed curves 406 and 412) is toward the right (of the solid curve 408 and 414 respectively).

However, when the charge on the Neutravidin protein (target molecule 255) is positive, the shift of the dashed curve (e.g., dashed curve 402) is to the left (of the solid curve 404).

Continuing with the flow chart 300 in FIG. 3B, the shift in capacitance versus voltage curves (C-V curves) at or near flatband capacitance are measured (e.g., as the shift along the voltage axis between the C-V curves of the solid lines and the respective dashed line at each individual pH value) after addition of Neutravidin protein, and this shift is referred to as the change in flatband voltage ($\delta V_{fb}$) at block 310. One skilled in the art understands flatband capacitance and flatband voltage as discussed herein.

Figure 5:
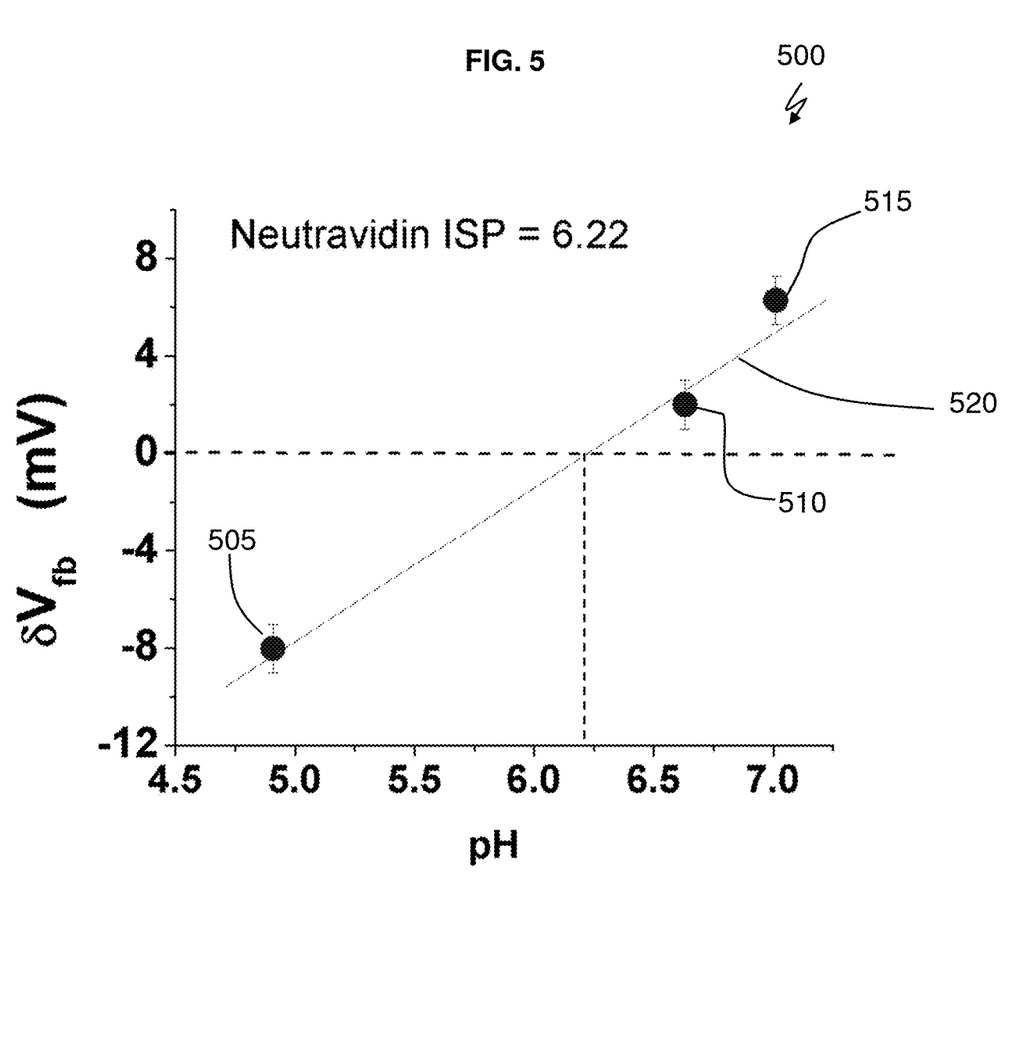
FIG. 5 is a graph of capacitance versus voltage curves plotted as a function of different pH values of an eclectically conductive solution according to an embodiment.

At block 312, the measured $\delta V_{fb}$ voltage values on the y-axis are plotted versus pH values of the solution 225 (that were tested) on the x-axis, and the data is fitted with a linear fit below as shown in FIG. 5.

At block 314, the linear fit to the data is used (e.g., by the computer 250) for extrapolating the pH value that corresponds to $\delta V_{fb}=0$ (i.e., the shift/difference between the dashed lines and solid lines in FIG. 4 is 0 for the target molecule 255). This extrapolated pH value is the measure of the isoelectric point of Neutravidin protein.

FIG. 5 is a graph 500 of the C-V curve plotted as a function of pH values of the electrically conductive solution 225 on the x-axis (which may be performed by the computer 250) versus change in flatband voltage (i.e., shift between curves 402 and 404, curves 406 and 408, and curves 42 and 414, respectively) on the y-axis. Each symbol/point 505, 510, and 515 is measured data from C-V curves 405, 410, and 415.

In FIG. 5, the flatband voltages (WO in for the data points 505, 510, and 515 are estimated at a fixed capacitance close to the flatband capacitance (CO value. In the example test measurement, $C_{fb}=12$ nF (nanofarads). For data point 505, the magnitude (shown as a magnitude of approximately 8 mV) of $\delta V_{fb}$ is the capacitance versus voltage curve shift along x-axis taken from FIG. 4. When the dashed curve shifts left with respect to the solid curve, then $\delta V_{fb}$ is assigned a negative value. Accordingly, the flatband voltage of data point 505 is approximately –8 mV in FIG. 5.

For data point 515, the magnitude (shown as a magnitude of approximately 7.2 mV) of $\delta V_{fb}$ is the C-V curve shift along the x-axis taken from FIG. 4. When the dashed curve shifts right with respect to the solid curve, then $\delta V_{fb}$ is assigned a positive value. Accordingly, the flatband voltage of data point 515 is approximately +7.2 mV.

Once the symbols/points are plotted in the graph 500, a line 520 that is a linear fit to the symbols/points 505, 510, and 515 is applied. From the linear fit shown by line 520, the flatband voltage shift is zero when the pH is the value 6.22. Accordingly, the estimated Neutravidin protein isoelectric point is pH value 6.22 which compares good to a 6.3 pH value measured by conventional methods.

It is noted that the process for determining the isoelectric point of the molecule 255 may be manual, semiautomatic, and/or automatic via the capacitor device 200 and electronic equipment 250. Pumps and reservoirs may be added and controlled by the electronic equipment 250 (and/or operator) to automatically measure the capacitance for a pH value, flush the solution 225, add the molecule 255, and measure the capacitance with the molecule 255 present. The electronic equipment 250 can be configured to continuously perform measurements with (i.e., bound to the functionalized material 235 of the dielectric layer 215) and without the molecule 255 in the solution 225 until every desired pH value has been tested.

As discussed herein, the embodiment demonstrates a better method for measuring the isoelectric point of a protein (or any molecule 255). The target protein has to bind to the dielectric surface, and this can be achieved by functionalizing the surface. In a case where the sample solution contains many different types of proteins, the dielectric surface has to be functionalized such that it would specifically bind target protein. In the case where the sample solution contains only the target proteins, then the surface should be functionalized for non-specific binding.

Figure 6:
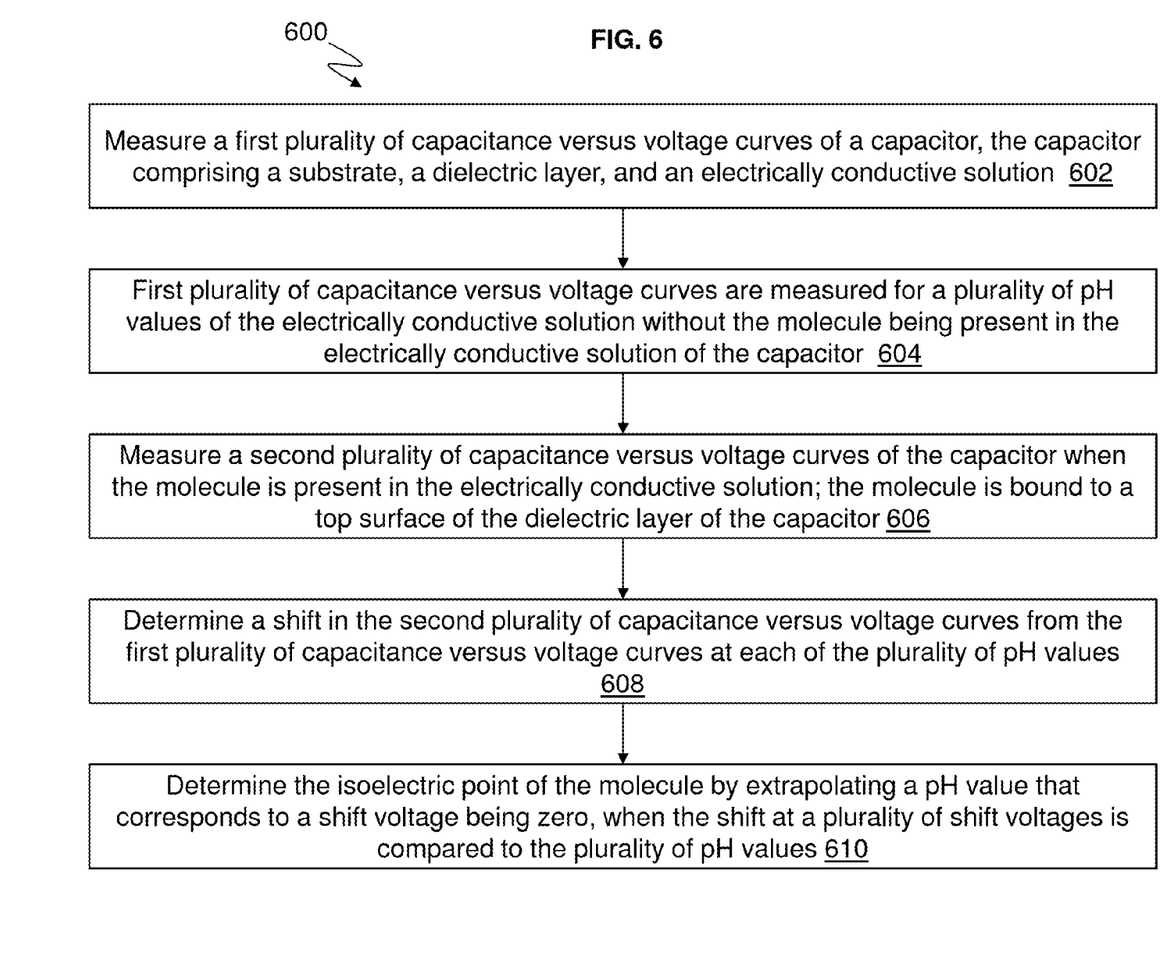
FIG. 6 is a method of determining an isoelectric point of a molecule according to an embodiment.

FIG. 6 is a method 600 of determining an isoelectric point of a molecule 255 according to an embodiment. Reference can be made to FIGS. 1-5 and 7.

At block 602, a first plurality of capacitance versus voltage curves (such as, e.g., solid curves 404, 408, 414) of a capacitor device 200 are measured by the electronic equipment 250 (e.g., test setup equipment), and the capacitor device 200 includes a substrate 205, a dielectric layer 230, and an electrically conductive solution 225.

The first plurality of capacitance versus voltage curves are measured (via computer 250) for a plurality of pH values (e.g., pH values 6.9, 6.3, 4.7) of the electrically conductive solution 225 without the molecule 255 being present in the electrically conductive solution 225 of the capacitor device 200 at block 604.

At block 606, a second plurality of capacitance versus voltage curves (such as, e.g., dashed curves 402, 406, 412) of the capacitor device 200 are measured by the computer 250 when the molecule 255 is present in the electrically conductive solution 225, and the molecule 255 is bound to a top surface (e.g., bound to the functionalized material 235) of the dielectric layer 230 of the capacitor device 200.

A shift in the second plurality of capacitance versus voltage curves from the first plurality of capacitance versus voltage curves is determined/measured by the computer 250 at each of the respective pH values (pH values 6.9, 6.3, 4.7) at block 608.

The isoelectric point of the molecule is determined (by the computer 250) by extrapolating a pH value (such as, e.g., 6.22 in FIG. 5) that corresponds to a shift voltage being zero (e.g., the change in flatband voltage $\delta V_{fb}$ is 0), when the shift voltage at a plurality of shift voltages (e.g., voltages on the y-axis) is compared to the plurality of pH values (e.g., pH values on the x-axis).

The method in which the first plurality of capacitance versus voltage curves of the capacitor device 200 are measured through a first contact 240 electrically connected to the electrically conductive solution 225 and a second contact 245 electrically connected to the substrate 205 of the capacitor device 200.

The method in which the second plurality of capacitance versus voltage curves of the capacitor device 200 are measured through the first contact 240 electrically connected to the electrically conductive solution 225 and the second contact 245 electrically connected to the substrate 205 of the capacitor device 200.

The method in which determining the shift in the second plurality of capacitance versus voltage curves from the first plurality of capacitance versus voltage curves at each of the plurality of pH values is implemented by determining a change in flatband voltage between each of the first plurality of capacitance versus voltage curves and the second plurality of capacitance versus voltage curves at each of the plurality of pH values (e.g., by the computer 250).

The method in which determining the isoelectric point of the molecule by extrapolating the pH value that corresponds to the shift voltage being zero is implemented by plotting points (e.g., points 505, 510, 515) for the plurality of shift voltages versus the plurality of pH values (by the computer 250). The method includes applying a linear fit as a line (e.g., the line 520) fitting the points plotted for the plurality of shift voltages versus the plurality of pH values. The method includes determining (e.g., by the computer 250) the isoelectric point of the molecule 255 as the pH value at which the line 520 crosses the shift voltage equals zero.

In the method, the plurality of shift voltages correspond to a change in flatband voltage at each of the plurality of pH values tested for the capacitor device 200. The functionalized material 235 (e.g., biotin) is applied on the top surface of the dielectric layer 230, and the functionalized material 235 is configured to bind to the molecule 255.

The dielectric layer 230 may have a bilayer of dielectric materials (e.g., dielectric layers 210 and 215), or the dielectric layer 230 may be a single dielectric material. In the method, the electrically conductive solution 225 is a top gate for terminal 240 of the capacitor device 200, and the substrate 205 is the body terminal 245 of the capacitor device 200.

In the method, the second plurality of capacitance versus voltage curves shift to the right (e.g., dashed curves 406 and 412) of the first plurality of capacitance versus voltage curves when the charge on the molecule 255 is negative with respect to the pH values being tested. Also, the second plurality of capacitance versus voltage curves shift to the left (e.g., dashed curve 402) of the first plurality of capacitance versus voltage curves when the charge on the molecule 255 is positive with respect to pH values being tested.

Further, regarding the electronic equipment 250 (e.g., as the computer test setup equipment for testing and analysis), the electronic equipment 250 may implement one or more voltage sources and may implement, control, and/or regulate the voltages applied by the voltage source connected to the device 200. The electronic equipment 250 may implement test equipment to control and/or regulate capacitance measurements and current (current) measurements (for various applied voltages) as understood by one skilled in the art.

Various methods, procedures, modules, flow diagrams, tools, applications, circuits, elements, and techniques discussed herein may also incorporate and/or utilize the capabilities of the electronic equipment 250. One or more of the capabilities of the electronic equipment 250 may be utilized to implement, to connect to, and/or to support any element discussed herein (as understood by one skilled in the art) in FIGS. 1-6. For example, the electronic equipment 250 may be any type of test equipment including voltage sources, ammeters, capacitance meters, etc., for testing and analysis discussed herein. The electronic equipment 250 may include and/or be coupled to the cables, plugs, wires, electrodes, patch clamps, etc. The electronic equipment 250 may include a processing circuit to execute instructions according to the method discussed herein.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated The flow diagrams depicted herein are just one example. There may be many variations to this diagram or the steps (or operations) described therein without departing from the spirit of the invention. For instance, the steps may be performed in a differing order or steps may be added, deleted or modified. All of these variations are considered a part of the claimed invention.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

What is claimed:

1. A system for determining an isoelectric point of a target molecule, the system comprising:
   a dielectric layer disposed on a substrate;
   a functionalized material on the dielectric layer;
   an electrically conductive solution on the dielectric layer, the substrate, the dielectric layer, and the electrically conductive solution forming a capacitor;
   a first contact in the electrically conductive solution and a second contact on the substrate;
   wherein a first plurality of capacitance versus voltage curves of the capacitor are measured via the first contact and the second contact;
   wherein the first plurality of capacitance versus voltage curves are measured for a plurality of pH values of the electrically conductive solution without the target molecule being present in the electrically conductive solution of the capacitor;
   wherein a second plurality of capacitance versus voltage curves of the capacitor are measured via the first contact and the second contact when the target molecule is present in the electrically conductive solution, the target molecule being bound to the functionalized material on a top surface of the dielectric layer of the capacitor;
   wherein a shift in the second plurality of capacitance versus voltage curves from the first plurality of capacitance versus voltage curves is determined at each of the plurality of pH values via test equipment; and
   wherein the isoelectric point of the target molecule is determined via the test equipment by extrapolating a pH value that corresponds to a shift voltage being zero, when the shift at a plurality of shift voltages is compared to the plurality of pH values.

2. The system of claim 1, wherein determining the isoelectric point of the target molecule by extrapolating the pH value that corresponds to the shift voltage being zero comprises plotting points for the plurality of shift voltages versus the plurality of pH values via the test equipment.

3. The system of claim 2, wherein a linear fit is applied as a line fitting the points plotted for the plurality of shift voltages versus the plurality of pH values via the test equipment.

4. The system of claim 3, wherein the isoelectric point of the target molecule is determined to be the pH value at which the line crosses the shift voltage equals zero.

5. A non-transitory computer program product for determining an isoelectric point of a target molecule, the computer program product comprising a computer readable storage medium having program code embodied therewith, the program code executable by a processing circuit to perform a method comprising:

measuring a first plurality of capacitance versus voltage curves of a capacitor, the capacitor comprising a substrate, a dielectric layer, and an electrically conductive solution;

wherein the first plurality of capacitance versus voltage curves are measured for a plurality of pH values of the electrically conductive solution without the target molecule being present in the electrically conductive solution of the capacitor;

measuring a second plurality of capacitance versus voltage curves of the capacitor when the target molecule is present in the electrically conductive solution, the target molecule being bound to a top surface of the dielectric layer of the capacitor;

determining a shift in the second plurality of capacitance versus voltage curves from the first plurality of capacitance versus voltage curves at each of the plurality of pH values; and determining the isoelectric point of the target molecule by extrapolating a pH value that corresponds to a shift voltage being zero, when the shift at a plurality of shift voltages is compared to the plurality of pH values.

* * * * *